United States Patent [19]

Toda et al.

[11] Patent Number: 4,862,729
[45] Date of Patent: Sep. 5, 1989

[54] METHOD FOR MEASURING THE AMOUNT OF GAS CONTAINED IN LIQUID

[75] Inventors: Kenichi Toda; Tetsuhiro Hori, both of Okazaki, Japan

[73] Assignee: Kabushiki Kaisha Polyurethan Engineering, Tokyo, Japan

[21] Appl. No.: 220,703

[22] Filed: Jul. 13, 1988

Related U.S. Application Data

[62] Division of Ser. No. 948,173, Dec. 31, 1986, abandoned.

[30] Foreign Application Priority Data

Sep. 26, 1986 [JP] Japan .................. 61-228568

[51] Int. Cl.[4] ............................................ G01N 7/00
[52] U.S. Cl. ................................................... 73/19
[58] Field of Search ................. 73/61 R, 19; 251/324; 55/270

[56] References Cited

U.S. PATENT DOCUMENTS

| | | | |
|---|---|---|---|
| 2,138,141 | 11/1938 | Cromer et al. | 73/19 |
| 2,680,060 | 6/1954 | Natelson | 73/38 |
| 2,798,690 | 7/1957 | Nelson et al. | 251/324 X |
| 2,817,955 | 12/1957 | Mercier | 251/324 X |
| 3,521,478 | 7/1970 | Magorien | 73/19 |
| 3,731,530 | 5/1973 | Tanguy et al. | 73/61 R |
| 3,968,678 | 7/1976 | Krener et al. | 73/19 |
| 4,120,192 | 10/1978 | Williamson | 73/19 |
| 4,164,137 | 8/1979 | Williamson | 73/19 |
| 4,255,088 | 3/1981 | Newton et al. | 73/19 X |
| 4,329,869 | 5/1982 | Toda | 73/19 |

*Primary Examiner*—Hezron E. Williams
*Attorney, Agent, or Firm*—Armstrong, Nikaido, Marmelstein, Kubovcik & Murray

[57] ABSTRACT

A method for measuring the amount of the gas contained in liquid, comprising introducing a liquid material into a vacuum measuring chamber, changing the volume of the measuring chamber to provide two different liquid pressures of the liquid material in the measuring chamber, detecting the different pressures to measure the amount of gas on the basis of Boyle's law.

3 Claims, 4 Drawing Sheets

METHOD FOR MEASURING THE AMOUNT OF GAS CONTAINED IN LIQUID

This is a division of application Ser. No. 948,173, filed Dec. 31, 1986, now abandoned.

1. Field of the Invention

The present invention relates to a method for measuring the amount of gas contained in liquid.

2. Description of the Related Art

For example, when a polyurethan resin is foamed and molded, a liquid material of polyurethane resin is mixed with a dry air or nitrogen gas or the like to obtain a uniform cell construction.

The amount of gas to be introduced into the liquid material must be controlled in accordance with precise measurements of the amount of gas, since quality and property of the molded products largely depend on the amount of gas contained in the liquid material.

U.S. Pat. No. 4,329,869 which has the same assignee as the present application discloses a method for measuring the amount of air bubbles contained in liquid. In this known measuring method disclosed in U.S. Pat. No. 4,329,869, the liquid material containing air bubbles (gas) to be measured is first compressed to provide two optional and different volumes of liquid, and then, a change in pressure of gas contained in the two volumes of liquid is measured by means of a pressure gage to determine the amount of gas, in accordance with Boyle's law.

It is, however, impossible or next to impossible to measure a small amount of gas contained in liquid, for example, less than 15% (mixing ratio). This is because such a small amount of gas can easily be dissolved into liquid or liquefied. The amount of liquefied or dissolved gas can not be measured by a known measuring method, as disclosed in U.S. Pat. No. 4,329,869 mentioned above.

The primary object of the present invention is, therefore, to provide a measuring method of gas contained in liquid, which makes it possible to measure a small amount of gas contained in liquid even when gas is dissolved into liquid or is liquefied.

In order to achieve the object of the invention mentioned above, according to the present invention, there is provided a measuring method of gas contained in liquid, in which a liquid to be measured is introduced and enclosed in a vacuum measuring chamber, and then, the volume of the measuring chamber is changed to provide two different volume conditions of liquid to be measured, so that two different liquid pressures can be measured to detect the amount of gas contained in liquid.

With the method of the invention mentioned above, the liquid to be measured can be rapidly introduced into the measuring chamber which is maintained vacuum, due to a pressure difference, so that the gas which is dissolved into liquid or liquefied can be gasified. Consequently, the gas which has been dissolved into liquid appears in a liquid phase.

The gas is introduced in the vacuum measuring chamber and then the volume of the chamber is changed so that only the gas changes its volume, since the liquid is a noncompressible fluid. Accordingly, the two different volumes of the measuring chamber and the corresponding two different liquid pressures are measured to precisely and easily detect the amount of gas contained in liquid to be measured. It will be appreciated that it takes a very long time before the gasified gas dissolves and liquefies again, in comparison with the time necessary for measuring.

BRIEF DESCRIPTION OF THE DRAWINGS

The invention will be described below in detail, with reference to the accompanying drawings, in which.

DETAILED DESCRIPTION OF PREFERRED EMBODIMENTS

Figure 1:
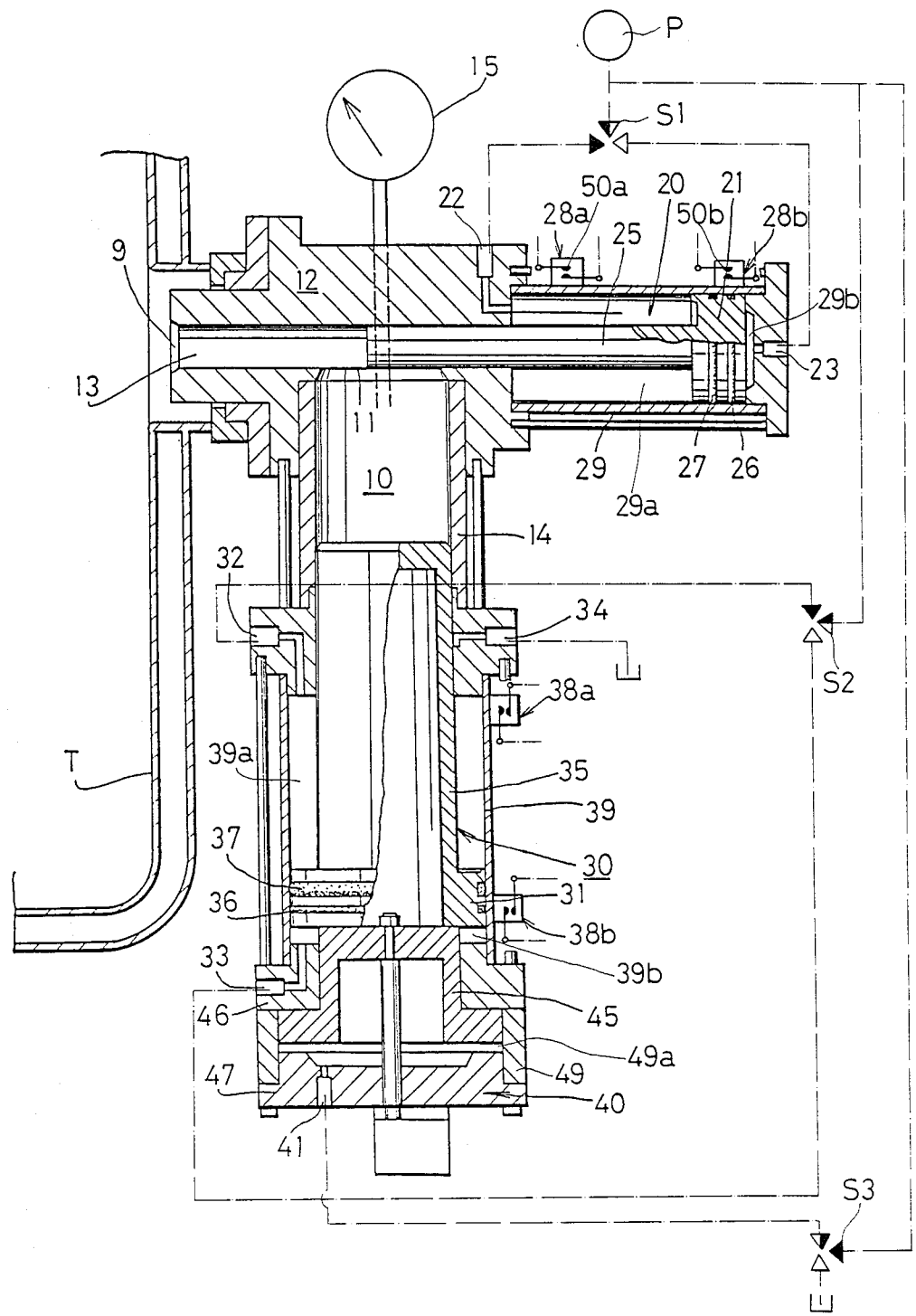
FIG. 1 is an enlarged longitudinal sectional view of a measuring apparatus which can be used to carry out the present invention.

A measuring apparatus which can be used to measure the amount of gas contained in liquid, according to the present invention, shown in FIG. 1 is connected to a part of a tank T which contains a liquid material to be measured, such as liquid polyurethan resin, so that the liquid material can be introduced into the measuring apparatus when sampling is necessary. The apparatus has a body 12 which has therein a measuring chamber 10, a valve device 20 for selectively closing the measuring chamber 10, and main and auxiliary hydraulic devices 30 and 40.

The measuring chamber 10 has an opening 11 which is connected to the tank T through an inlet port 9 and an inlet passage 13 which are formed in the body 12.

The apparatus also has a pressure gage 15 which detects a liquid pressure in the measuring chamber 10. The numeral 14 designates a cylindrical wall which is inserted in the body 12 to define the measuring chamber 10.

The valve device 20 has a piston rod 25 which axially slides in the inlet passage 13 to open and close the opening 11 of the measuring chamber 10. In the illustrated embodiment, the piston rod 25 moves in the left hand direction to completely close the opening 11. The valve device 20 has a hydraulic cylinder 29 having cylinder chambers 29a and 29b in which a piston integral with the piston rod 25 moves in the axial directions. The piston 21 in the illustrated embodiment is of double acting type, in which the cylinder chambers 29a and 29b are connected to a pressure source, such as a pneumatic pump P through a directional control valve S1 per se known, by means of cylinder ports 22 and 23, respectively. When the hydraulic connection is established between the cylinder chamber 29a and the air pump P, the piston 21 moves in the right hand direction in FIG. 1, and when the hydraulic connection between the cylinder chamber 29b and the air pump P is established, the piston 21 moves in the left hand direction in FIG. 1. The piston 21 is provided, on its outer periphery, with a magnet 26 which actuates detectors 28a and 28b which are made of, for example, reed switches 50a and 50b which are made ON, as is well known, by the magnetic force.

Namely, when the magnet 26 is located in the vicinity of the reed switch 50a, the reed switch 50a is made ON and when the magnet 26 is in the vicinity of the reed switch 50b, the read switch 50b is made ON. The detector 28a detects that the opening 11 of the measuring chamber 10 is closed, i.e. closed position of the valve device 20 and the detector 28b detects that the opening 11 is open, i.e. an open position of the valve device 20. Preferably, the magnet 26 is a rubber magnet, so that it also serves as a seal member of the piston 21. The numeral 27 designates an additional seal member, such as an O-ring.

A main cylinder device 30 has a cylinder 39 in which a piston 31 having a piston rod 35 moves upward and downward in FIG. 1. The piston rod 35 projects into the measuring chamber 10 to change an effective volume of the liquid material contained in the measuring chamber 10. The cylinder device 30 is constructed in a similar way to the hydraulic cylinder device of the valve device 20. Namely, the cylinder 39 defines two cylinder chambers 39a and 39b which are connected to the air pump P through a second directional control valve S2, by means of cylinder ports 32 and 33, respectively. The numeral 34 designates a drain port. The double acting piston 31 has a magnet 36 which is preferably a rubber magnet, on its outer periphery. The piston 31 is sealed by a seal member 37, such as an O-ring. The position of the magnet 36, i.e. the position of the piston 31 can be detected by detectors 38a and 38b which actuate in response to the displacement of the magnet 36 and which are formed in the same fashion as the detectors 28a and 28b as mentioned above.

An auxiliary hydraulic cylinder device 40 is located in rear of, i.e. below the main hydraulic cylinder device 30 is FIG. 1 to limit the retracted position of the piston 31 of the main cylinder device 30. In the illustrated embodiment, the auxiliary cylinder device 40 has an upper cylinder 46 which is connected to the cylinder 39 and a lower cylinder 47 which is secured to the upper cylinder 46 by means of an intermediate cylinder 49. A piston 45 moves up and down in FIG. 1 in a cylinder space defined by the cylinders 46, 47, and 49. The piston 45 is a single acting piston, so that it selectively occupies an upper position in which the piston 45 comes into contact with the upper cylinder 46 which also serves as a upper stop of the piston 45, and a lower position in which the piston 45 comes into contact with the lower cylinder 47 which also serves as a lower stop of the piston 45. A cylinder chamber 49a which is defined by and in the lower and intermediate cylinders 47 and 49 is connected to the air pump P through a third directional control valve S3, by means of a cylinder port 41. The auxliary piston 45 is brought to the upper position when the cylinder chamber 49a communicates with the air pump P.

Figure 2:
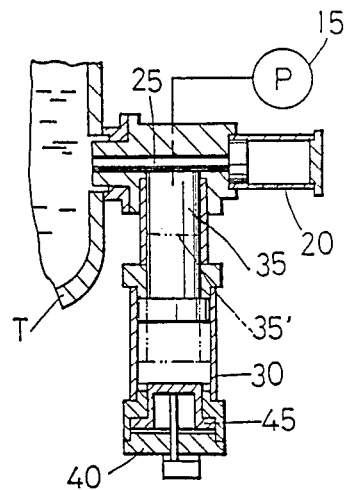
FIG. 2 is a sectional view of a main part of the measuring apparatus shown in FIG. 1, explaining how to establish a vacuum state in a measuring chamber.

The main piston 31 is positioned at an upper position in which the piston rod 35 in the measuring chamber 10 comes to its uppermost position in FIG. 1 before the measuring operation is carried out, as shown in FIG. 2. When measuring is effected, the main cyinder device 30 is actuated, so that the piston rod 35 thereof comes to a lower position 35', shown in FIG. 2, resulting in an establishment of vacuum in the measuring chamber 10.

Figure 3:
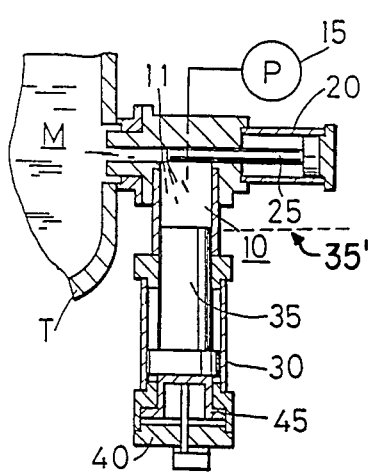
FIG. 3 is a sectional view similar to FIG. 2, explaining an introduction process of liquid to be measured into the measuring chamber.

After that, sampling of the liquid material is effected. That is, the liquid material M (polyurethan resin) in the tank T is introduced into the measuring chamber which is now maintained at vacuum through the port 9, inlet passage 13 and the opening 11 by operating the valve device 20, so that the piston rod 25 of valve device 20 moves in the right hand direction in FIG. 1 to occupy the open position of the valve device 20, as shown in FIG. 3. It should be borne in mind that the introduction of the liquid material M into the measuring chamber 10 rapidly takes place due to a large pressure difference between the tank T and the vacuum measuring chamber 10, so that the gas which is dissolved or liquefied in the liquid can be completely gasified. Alternatively, it is also possible to retract the piston rod 35 of the main piston 31 at a higher speed than that of the flow speed of the liquid material M into the measuring chamber 10, in order to introduce the liquid material M into the measuring chamber 10 while actuating the main cylinder device 30 without bringing in advance the piston rod 35 to the lower position 35' prior to the introduction of the liquid material M.

When the measuring chamber 10 is filled with the liquid material M, the valve device 20 operates, so that the piston rod 25 of the valve device 20 moves forward, i.e. in the left hand direction in FIG. 1 to close the opening 11 of the measuring chamber 10. Thus, the liquid material M is enclosed in the measuring chamber 10. The movement of the piston rod 25 to the valve closed position can be detected by the detector 28a. Further, the operation of the valve device, i.e. the movement of the piston 21 is commenced in response to the output signal of the detector 38b which detects the lower position of the main piston 31.

Figure 4:
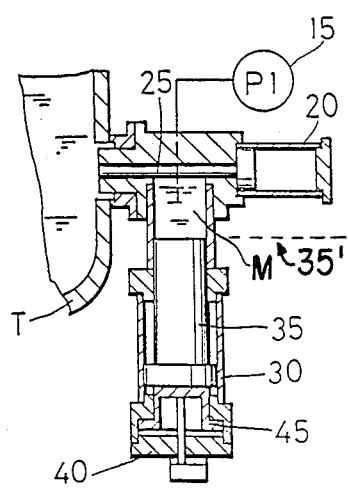
FIG. 4 is a sectional view showing a first measuring process.

Then, a first measuring is effected to detect the present P1 of the liquid material M enclosed in the measuring chamber 10, by means of a pressure gage 15 which is per se known and which is hydraulically connected to the measuring chamber 10, as shown in FIG. 4.

Figure 5:
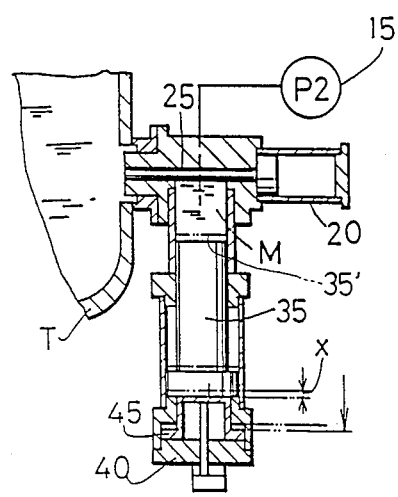
FIG. 5 is a sectional view showing a second measuring process, in which an auxiliary hydraulic device has a retracted piston.

After that, the second measuring is effected, as shown in FIG. 5. Namely, the piston rod 35 is moved by a slight distance by the auxiliary cylinder device 40. The lower position of the piston 31 of the main cylinder device 30 is restricted by the auxiliary piston 45, as mentioned before, and accordingly the axial movement of the auxiliary piston 45 causes the axial movement of the main piston 31. In FIG. 5, the auxiliary piston 45 which is initially located at the upper position is moved down, namely is retracted, to slightly move the main piston 31 downward, as shown in FIG. 5. The downward movement, i.e. the retraction of the auxiliary piston 45 takes place when the hydraulic pressure in the cylinder chamber 49a is released. On the contrary, if the auxiliary piston 45 initially occupies the lower position (retracted position), the auxiliary piston 45 is moved forward, i.e. upward by feeding the hydraulic pressure (air) into the cylinder chamber 49a, in order to cause a slight axial displacement of the main piston 31. After the slight axial movement of the main piston 31 which makes a different volume of measuring chamber 10 occurs, the pressure P2 in the measuring chamber 10 is detected by the pressure gage 15. The amount A(%) of gas contained in the liquid material M can be obtained by the following equation which can be derived from Boyle's law, $A(\%) =$ $$\frac{P1 \cdot P2 \cdot L \cdot D}{1.033(V(P1 - P2) - P2 \cdot L \cdot D) + P1 \cdot P2 \cdot L \cdot D} \times 100$$

wherein $L$(cm) is an axial displacement of the main piston 31 between positions shown in FIGS. 4 and 5, i.e. the axial displaceent of the auxiliary piston 45;

$D$(cm$^2$) is a sectional area of the main cylinder chamber 39a;

$V$(cm$^3$) is a volume of the measuring chamber 10 at the lower position 35' of the main piston rod 35.

Figure 6:
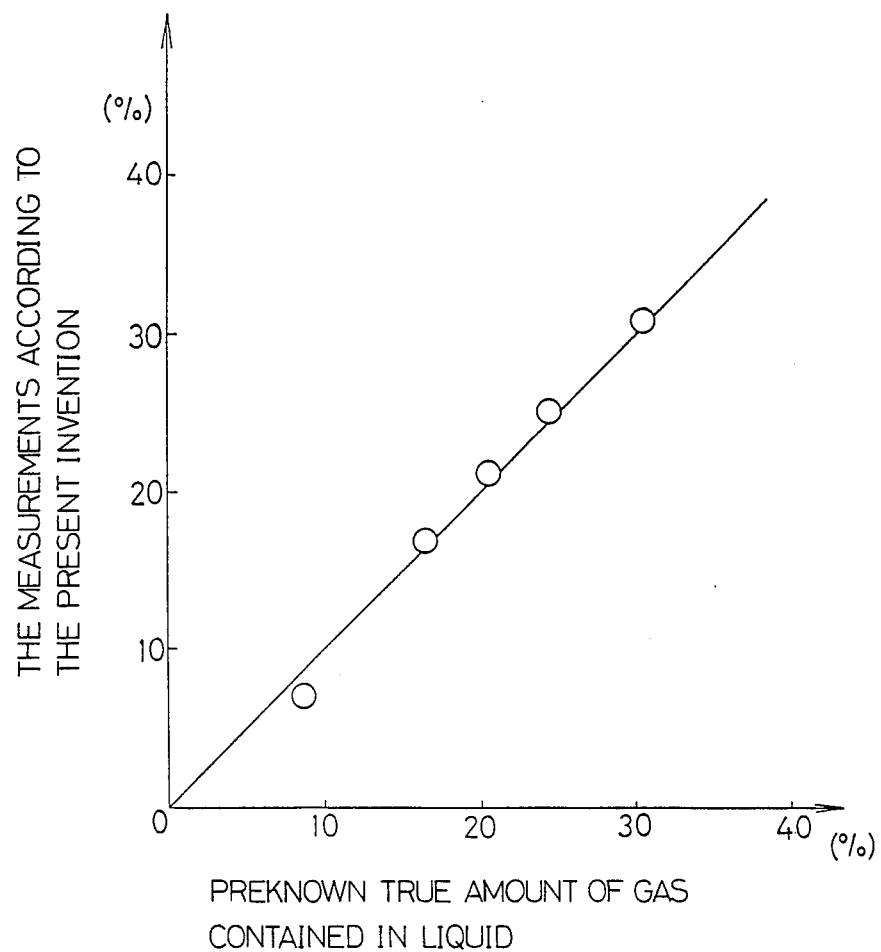
FIG. 6 is a diagram showing measurements of the amount of gas contained in liquid, according to the present invention; and, FIG. 7 is a diagram showing measurments of the amount of gas contained in liquid, according to the prior art.

The experimental results of measurements according to the present invention are shown in FIG. 6.

In FIG. 6 an ordinate represents the amount A (%) of gas contained in liquid, detected by a masuring method according to the present invetion, and an abscissa represents preknown true amount of gas (%) contained in liquid.

Figure 7:
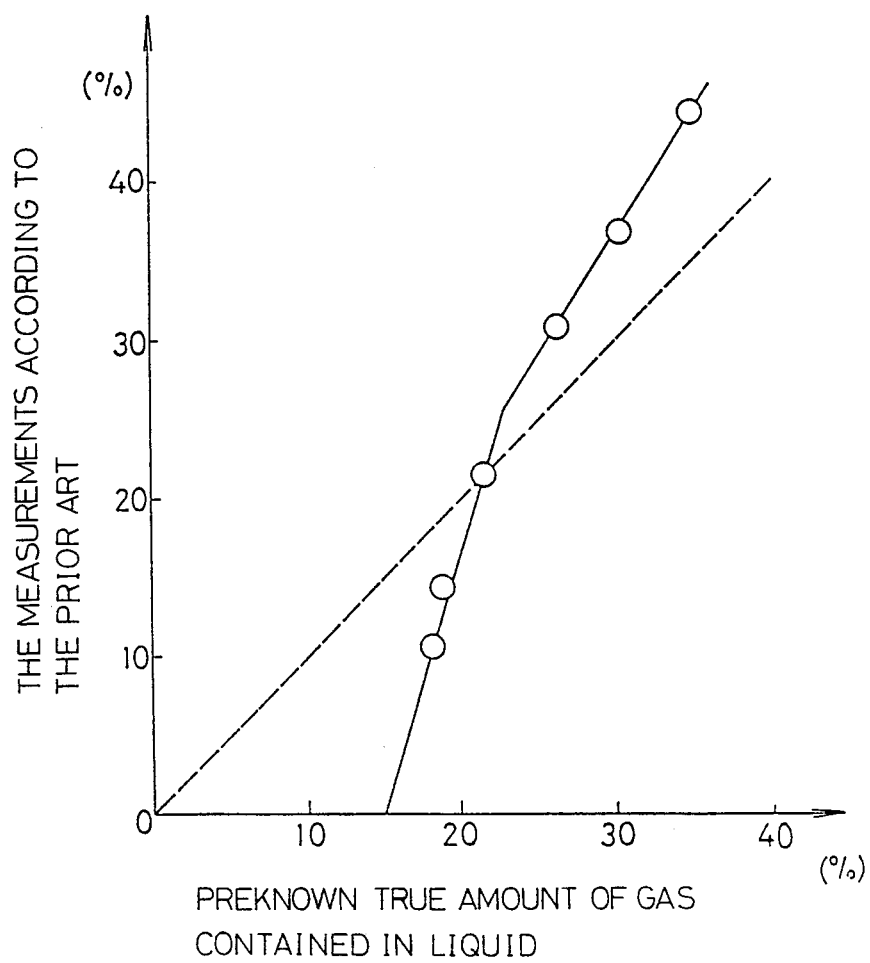

As can be seen in from FIG. 6, the measurment and the true amount of gas (true value) have a substantially proportional relationship and substantially same values. FIG. 7 shows the measurement according to the prior art. It will be easily seen from FIG. 7 that when the amount of gas is less than 20%, the measurement values are largely different from and smaller than the true values, according to the prior art.

As can be understood from the above discussion, according to the present invention, the measuring chamber is maintained vacuum during sampling of the liquid material, and accordingly a precise gas measuring condition can be established. Furthermore, according to the present invention, the dissolved or liquefied gas can be substantially completely gasified when the liquid material is introduced into the measuring chamber at a very high speed due to the pressure difference, and accordingly, the amount of gas contained in the liquid matreial can be accurately measured.

In particular, according to the present invention, the gasification of the dissolved or liquefied gas takes place at the same step of introduction of the liquid material into the measuring chamber, resulting in a simple and effective measuring process.

The precise measurement of the amount of gas contained in liquid contributes to a precise control of the amount of gas to be contained in the liquid material.

We claim:

1. An apparatus for measuring the amount of gas contained in a liquid material comprising:
   (1) a cylindrical measuring chamber (10);
   (2) an inlet part (9,13) connecting said measuring chamber to a sample source;
   (3) a valve device (20) comprising means for closing said measuring chamber from said inlet part;
   (4) a piston (31) fitted into said measuring chamber (10);
   (5) a first means for moving said piston a predetermined distance in said measuring chamber said comprising at least two cylindrical ports separated by a seal member on said piston, said cylinder ports being positioned so that said first means effects movement of said piston over the length of said measuring chamber;
   (6) a pressure gauge (15) connected to said measuring chamber;
   (7) a second means for moving said piston a predetermined distance in said measuring chamber; and
   (8) means for detecting the location of said valve means and said piston.

2. An apparatus according to claim 1 wherein said valve device comprises a housing having a cylindrical bore and a tubular member slidably disposed therein.

3. An apparatus according to claim 1 wherein said second means for moving said piston comprises a cylinder (45) disposed at a base of said piston, a chamber (40a) at the base thereof, an inlet and an outlet connected to said chamber, and a stop (46) which limits the travel of said cylinder.

* * * * *